(12) United States Patent
Reierson

(10) Patent No.: US 6,329,322 B1
(45) Date of Patent: Dec. 11, 2001

(54) HYBRID IONIC PHOSPHORUS SURFACTANT ADJUVANTS FOR BIOACTIVE COMPOSITIONS

(75) Inventor: Robert Lee Reierson, West Windsor, NJ (US)

(73) Assignee: Rhodia Inc., Cranbury, NJ (US)

( * ) Notice: Subject to any disclaimer, the term of this patent is extended or adjusted under 35 U.S.C. 154(b) by 0 days.

(21) Appl. No.: 09/624,933

(22) Filed: Jul. 25, 2000

Related U.S. Application Data
(60) Provisional application No. 60/145,719, filed on Jul. 27, 1999.

(51) Int. Cl.$^7$ .................................................. A01N 57/18
(52) U.S. Cl. ........................... 504/206; 504/365; 514/937
(58) Field of Search ................................... 504/206, 365; 514/937

(56) References Cited

U.S. PATENT DOCUMENTS

| | | | |
|---|---|---|---|
| 4,657,581 | * | 4/1987 | Takematsu et al. ................... 71/118 |
| 5,550,274 | * | 8/1996 | Reierson ............................... 558/110 |
| 5,554,781 | * | 9/1996 | Reierson ............................... 558/110 |
| 5,846,923 | * | 12/1998 | Reierson ............................... 510/467 |
| 5,977,023 | * | 11/1999 | Inoue et al. ........................... 504/116 |

FOREIGN PATENT DOCUMENTS

| 0 243 872 | * | 4/1987 | (EP) |
| 1 470 712 | * | 4/1977 | (GB) |

* cited by examiner

*Primary Examiner*—S. Mark Clardy
(74) *Attorney, Agent, or Firm*—John A. Shedden

(57) ABSTRACT

Aqueous bioactive compositions having increased stability and enhanced bioefficacy comprising a bioactive compound, an effective amount of phosphate or phosphonate amphoteric surfactant having multiple ionic charges, and water. The preferred bioactive is a small ionic herbicide such as N-phosphonomethyl glycine or a salt thereof.

17 Claims, No Drawings

HYBRID IONIC PHOSPHORUS SURFACTANT ADJUVANTS FOR BIOACTIVE COMPOSITIONS

This application claims benefit of Provisional Application 60/145,719 filed Jul. 27, 1999.

FIELD OF THE INVENTION

This invention relates to the use of phosphate and phosphonate amphoteric surfactants having multiple ionic charges to increase the stability of bioactive compositions and enhance the bioefficacy of the active.

BACKGROUND OF THE INVENTION

Numerous organic bioactives, especially pesticides, i.e., chemicals that are useful in the control of insects, fungi, weeds, and the like have been developed in recent years. Regardless of whether the pesticide is inherently water soluble or water insoluble, it is desirable to use the same in an aqueous medium rather than in a non-aqueous solvent which is more difficult to use by the formulator and applicator, could cause environmental damage, is more costly and is in general, less desirable. Water-based dispersions, emulsions, and/or solutions can be prepared from most pesticides using selected surfactants. Proper selection of the surfactant can also improve the efficacy of pesticidal compositions.

Surfactants have proven to be especially useful in the preparation of herbicidal compositions whether the herbicide is water soluble or insoluble. When the herbicide is water insoluble, the surfactant can be used to make a water dispersible herbicide composition. When the herbicide is water soluble, the surfactant can often be used to improve the herbicidal effectiveness of the herbicidal composition.

One class of surfactants that has found much commercial success in the preparation of herbicidal compositions includes the polyoxyalkylene alkylamines. These compounds have the necessary surface activity so that many otherwise water insoluble herbicides, as well as water soluble herbicides, can be formulated into concentrates which will form useful dispersions, emulsions, and solutions in water. In addition, herbicides formulated into dispersions, emulsions, and solutions using these surfactants often have improved herbicidal properties.

However, while the polyoxyalkylene alkylamine compounds have excellent surfactant properties and often enhance the bioefficacy of phytotoxicants, they unfortunately are irritants, especially producing eye irritation and must be used with a high degree of caution.

Many efforts have been made to reduce the irritancy of the polyoxy alkylene alkylamine compounds while still retaining their surfactant effectiveness in stabilizing agricultural formulations and enhancing bioeffectiveness. Most of these efforts entail the addition of multiple surfactant compounds to the alkylamine—bioactive composition.

Perhaps the most widely used herbicide worldwide is glyphosate, which chemically is N-phosphonomethylglycine. This product is normally used in an agriculturally acceptable form, such as a water soluble salt, e.g., the isopropylamine salt. Often used surfactants for the preparation of glyphosate concentrates, which can then be diluted with water for use by the applicator, are the aforementioned polyoxyalkylene alkylamines, especially the ethoxylated tallow amines.

It is therefore an object of the present invention to provide stable surfactant containing bioactive compositions with enhanced bioeffectiveness.

Another object of the present invention is to provide stable pesticidal compositions, especially herbicidal compositions, and most especially those containing glyphosate, having agriculturally acceptable efficacy and reduced eye irritation.

Another object of the present invention is to provide new methods for controlling the growth of weeds and other vegetation.

Other objects of the present invention will become apparent from the following description.

SUMMARY OF THE INVENTION

The present invention is directed to bioactive compositions, particularly pesticidal compositions, and most particularly herbicidal compositions comprising a pesticide, such as a herbicide, and a surfactant composition comprising a phosphate or phosphonate amphoteric surfactant having multiple ionic charges. These compositions are readily dispersible in water so as to prepare extremely stable, aqueous compositions useful for, among other things, the control of weeds, insects, fungi, and the like in the absence of severe eye irritancy such as is associated with the use of the polyoxyalkylated alkylamine surfactants.

In accordance with a preferred embodiment of the present invention, an aqueous solution is provided which comprises a herbicidally effective amount of a glyphosate herbicide, either in acid or salt form, whose composition is stabilized and whose herbicidal effectiveness is enhanced by the presence of a potentiality effective amount of the phosphate or phosphonate amphoteric surfactant of the instant invention.

DETAILED DESCRIPTION OF THE INVENTION

The compositions of the instant invention comprise a bioactive, especially an ionic bioactive, and most especially a pesticidal polyionic bioactive and an effective amount of a phosphate or phosphonate amphoteric surfactant having multiple ionic charges. It has been discovered that these amphoteric surfactants increase the stability and enhance the bioeffectiveness of bioactives in aqueous compositions.

Amphoterics are, by definition, surfactants which, depending on the pH, can have anionic and/or cationic properties in aqueous medium. An amphoteric contains at least one acidic group and at least one basic group. The pH where these groups internally neutralize each other, producing a zwitterion (a cationic and anionic group in the same molecule), is called the isoelectric point (or isoelectric area). At pH above the isoelectric area, amphoterics act as anions and below the isoelectric area they act as cations with external counter ions (cations and anions, respectively).

The cationic functionality is generally a protonated secondary or tertiary amine group (in so-called weak nitrogen amphoterics), or a quaternary ammonium group (in strong nitrogen amphoterics or alkylbetaines). Weak nitrogen amphoterics are protonated only at lower pH levels whilst alkyl betaines retain their positive charge over virtually the whole pH range. At least one anionic group in the surfactant molecules of this invention is a phosphate or phosphonate moiety. Commonly and additionally other anionic groups such as a carboxylate, sometimes sulfonate or sulfate groups, and additional phosphate and/or phosphonate moieties are also present.

Amphoteric surfactants may have an equal or unequal number of anionic and cationic groups with the charge balanced by external counter ions. The number of such groups influences the isoelectric area, as does the ionic strength of such groups.

The primary source for the cationic functionality in the phosphate or phosphonate amphoterics of the instant invention is a nitrogen containing moiety. Preferably the moiety is an amine, an aminoalkyl, amido, aminoalkyl, amine oxide, or quaternary ammonium group.

Preferred phosphate or phosphonate amphoteric surfactant compositions useful in the instant invention are those of the formula:

$$
\begin{bmatrix} R_4\text{—}\begin{bmatrix} \overset{O}{\underset{R_5}{\overset{\parallel}{\text{OP}}}} \end{bmatrix}_w\text{—}(\text{OCHCH}_2)_{\overline{x}}\text{—}(C_nH_{2n})_y\text{—}X\text{—}\underset{Z_t}{\overset{R_1}{\text{N}}}\text{—}(C_nH_{2n})_{y'}\text{—} \end{bmatrix}
$$
$$
\begin{bmatrix} \underset{(CH_2CHO)_{x'}}{\overset{R}{|}}\text{—}\begin{bmatrix} \overset{O}{\underset{R_5}{\overset{\parallel}{\text{PO}}}} \end{bmatrix}_{w'}\text{—}Y \end{bmatrix} \quad \text{wherein X is}
$$
$$
\begin{bmatrix} \text{—}\underset{Z_{t'}}{\overset{R_2}{\text{N}}}\text{—}(C_nH_{2n})_{y''}\text{—}(CH_2CHO)_{x''}\text{—}\begin{bmatrix} \overset{O}{\underset{R_5}{\overset{\parallel}{\text{P}}}} \end{bmatrix}_v\text{—} \\ \text{—}\begin{bmatrix} \overset{O}{\underset{R_5}{\overset{\parallel}{\text{OP}}}} \end{bmatrix}_{v'}\text{—}(\text{OCHCH}_2)_{x'''}\text{—}(C_nH_{2n})_{y'''}\text{—} \end{bmatrix}_m .
$$

I $R_1$ and $R_2$ independently, are selected from the group consisting of substituted or unsubstituted $C_1$ to $C_{36}$ straight or branched chain alkyl, alkenyl, aryl, alkylaryl, arylalkyl and mixtures thereof, wherein said $R_1$ and $R_2$ are optionally further characterized as containing ether, thioether, polyoxyalkylene oxide, amine, amine oxide, quaternary ammonium, amide, alkylamine, alkylamide, carbonyl or ester groups, or are substituted thereby with open valences filled by $R_3$ wherein $R_3$ is hydrogen or $R_1$;

R independently is H, $C_{1-18}$ alkyl, alkenyl, aryl, alkaryl, or arylalkyl; optionally containing ether groups;

$R_4$ is independently H, $C_{1-18}$ alkyl, alkenyl, aryl, alkaryl, or arylalkyl;

$R_5$ is independently OH, OY, A, or $OR_4$ wherein A is

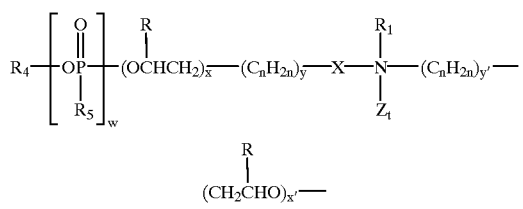

Y is H, or a counterion which, when needed to balance a charge, is an alkali metal, alkali earth metal, protonated amine, or quaternary ammonium counterion, Z is independently H, $C_{1-18}$ alkyl, alkenyl, aryl, alkylaryl, arylalkyl, or oxygen;

n is independently a whole number from 2 to about 4;

t and t' are independently 0 or 1;

m is 0 to 10;

v is 1 and v' is independently 0 or 1;

w and w' are independently 0, 1 or 2 with the proviso that both are not equal to 0;

x, x', x", and x'" are independently 0 to 50; and y, y', y", and y'" are independently 0 or 1.

More preferably, $R_1$ and $R_2$ individually are $$
-CH_2CH_2-\underset{\underset{R}{\overset{|}{(CH_2CHO)_zR_6}}}{N}-\overset{O}{\overset{\parallel}{C}}-R_2
$$

wherein $R_6$ is independently selected from the group consisting of H, or

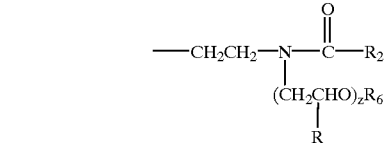

and z is 0 to 50.

Typical, and exemplary of the amphoteric surfactant formulae of this invention are the following:

$$
R_4\text{—}\underset{Z}{\overset{R_1}{\text{N}}}\text{—}(CH_2CHO)_{x'}\text{—}\overset{\overset{R}{|}}{\underset{R_5}{\overset{O}{\overset{\parallel}{P}}}}\text{—}O\text{—}Y
$$

II wherein:

w is 0, w' is 1, y and y' are 0, t is 1, m is 0, and x is 0; and

R, $R_1$, $R_4$, $R_5$, Z, Y, and x' are as defined above.

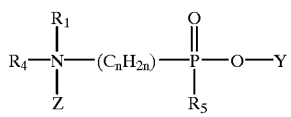

III wherein:

w is 0, w' is 1, x and x' are 0, y' is 0, y' is 1, t is 1, and m is 0; and $R_1$, $R_4$, $R_5$, Z, Y, and n are as defined above.

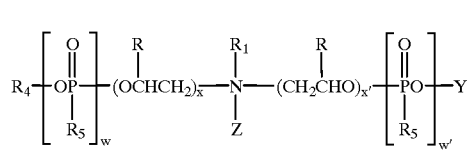

IV wherein:

y and y' are 0, m is 0, t is 1; and

R, $R_1$, $R_4$, $R_5$, Z, Y, w, w', x and x' are as defined above.

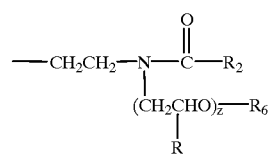

V wherein:

x and x' are 0, and m is 0; and $R_1$, $R_4$, $R_5$, Y, n, t, y and y' are as defined above.

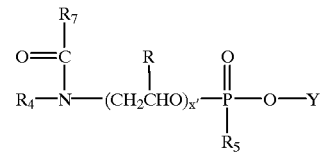

VI wherein:
$R_7$ is hydrogen or $C_1$–$C_{30}$ alkyl, alkenyl, aryl, alkaryl, or arylalkyl and thus, original $R_1$ contains $R_7$ and a carbonyl moiety,
w is 0, w' is 1, x is 0, y and y' are 0, m is 0, t is 0; and R, $R_4$, $R_5$, Y, and x' are as defined above.

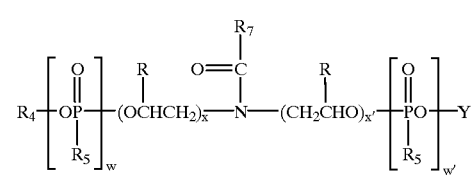

VII wherein:
y and y' are 0, t is 0, m is 0, and $R_1$ is $R_7$ and a carbonyl moiety; and
R, $R_4$, $R_5$, $R_7$, Y, x and x', and w and w' are as defined above.

Illustrative of a phosphate-linked, (poly)amphoteric within the scope of this invention is as follows:

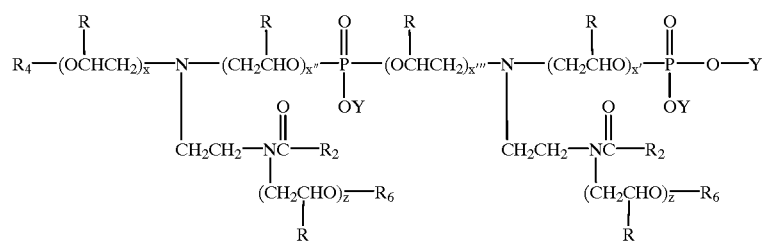

VIII wherein:
w is 0, w' is 1, m is 1, v' is 0, t and t' are 0, y, y', y", and y'" are 0, $R_5$ is —OY, and $R_1$ and $R_2$ are independently —CH$_2$CH$_2$—N(—C(=O)—$R_2$)(—(CH$_2$CHO)$_z$—$R_6$)(R)

wherein:
R, $R_4$, $R_2$, $R_6$, Y, x, x', x", and x'", and z are as defined above. These compounds are described in U.S. patent application Ser. No. 08/889,265 filed Aug. 7, 1997 and incorporated herein.

The preferred bioactives of this invention are the ionic bioactives that possess at least one ionic charge under conditions of use, i.e., at the pH of the aqueous medium during use. The preferred bioactives are the pesticides, especially the polyionic pesticides. The most preferred pesticides for use in the compositions of this invention are those that are small polyionic molecules, i.e. those having a molecular weight of less than about 300 g/mole. The very most preferred pesticides are the herbicidal actives such as N-phosphonomethyl glycine a.k.a. glyphosate and its salts such as the isopropylamine or trimethyl sulfonium salt (sulfosate); and 2-amino-4(hydroxymethylphosphinyl) butanoic acid (glufosinate).

By the term "stabilizingly effective amount" is meant that in a concentrated formulation of the bioactive in aqueous media i.e. from about 20 to about 70 percent by weight, no phase separation occurs over an extreme temperature storage range of from about 4° C. to about 55° C. over a period of three days, i.e. 72 hours.

The following Examples are provided by way of representation of the present invention and not by way of limitation.

EXAMPLE 1

Phosphation of Cocoamine POE-5 Bis-ethoxylate with 115% Polyphosphoric Acid

An oven dried apparatus consisting of a 1 L, 4-necked, round bottomed flask, a paddle stirrer, thermocouple, pressure equalizing addition funnel and a Claisen adaptor containing an argon gas inlet and outlet through a silicone oil filled bubbler tube was assembled while warm and flushed with argon for an hour with heating to provide a moisture free system. The flask was quickly charged with 402.88 g of Rhodameen C-5, a trademark of Rhodia Inc. For ethoxylated cocoamine, (0.99 mole) and the funnel with about 200 g 115% polyphosphoric acid. The stirred liquor was warmed to 52° C. in an oil bath and the acid was added over a three hour period. The heat of neutralization raised the temperature to 80° C. in the first hour so the bath was removed for an hour then returned as the temperature had dropped to 71° C. and stirring had become very difficult. The liquor temperature returned quickly to 77° C. and reached 88° C. by the end of the net addition of 197.65 g (2.320 mole). The liquor was heated to and maintained at 115° to 120° for four hours then allowed to cool to about 112°. Deionized water, 452.21 g, was added slowly through a fresh addition funnel over a four hour period as the liquor temperature was decreased gradually to 95° to balance the high liquor viscosity with the gentle boiling of the water as it was blended in. Heating at 95° was continued for an additional hour to complete the hydrolysis of the residual pyrophosphoric acid intermediates and obtain a clear, viscous, 57% solids solution.

Analysis of the solution by $^{31}P$ and $^{13}C$ nuclear magnetic resonance spectroscopy showed the phosphate product molar ratios to be 0.340 phosphoric acid, 0.623 monoalkyl phosphates and 0.036 dialkyl phosphates. Conversion of the alcohol groups was about 70%.

EXAMPLE 2

Phosphation of Cocoamine POE-5 Bis-ethoxylate with Hybrid Reagent

The process of Example 1 was repeated except that the phosphation was modified in accord with the technology described in U.S. Pat. Nos. 5,550,274 and 5,554,781.

The pre-dried 1 L flask was quickly charged under argon atmosphere with 304.01 g of Rhodameen C-5 ethoxylated cocoamine (0.751 mole) and the funnel with about 71.04 g 105% polyphosphoric acid (Rhodia Super Phos 105®). The stirred liquor was warmed to 40° C. by a thermostatically controlled infrared heat lamp and the acid was added over a 75 minute period. The heat of neutralization quickly raised the temperature to 50° C. (lamp off automatically) and the viscosity of the solution increased significantly as the salt formed, so the lamp thermocouple controller set point was raised to 60° C. The final temperature was 63° C.; total acid charge was 70.46 g (0.755 mole). The liquor was allowed to cool to about 54° C. while a predried pressure equalizing powder addition funnel with a screw feed system was charged with 92.24 g phosphoric anhydride and set in place of the acid addition funnel. The anhydride was added slowly, over a 135 minute period, to get good dispersion of the powder into the viscous solution. The temperature was held between 54° C. and 59° C. by periodic application of a room temperature water bath. Total charge of phosphoric anhydride was 91.24 g (0.321 mole). Upon completion of the addition, the viscous slurry was heated slowly by oil bath to 110° C. over a 210 minute period so that the liquor temperature remained close to that of the oil bath and stirring could be maintained. After seven hours, the temperature was allowed to cool to 100° C., nominally, and 298.81 g deionized water was added over a two hour period. Stirring was continued for another 45 minutes during which the temperature was decreased gradually to 95° C. to complete the hydrolysis of the residual pyrophosphoric acid intermediates and obtain a clear, viscous, 61% solids solution.

Analysis of the solution by $^{31}P$ and $^{13}C$ nuclear magnetic resonance spectroscopy showed the phosphate product molar ratios to be 0.365 phosphoric acid, 0.497 monoalkyl phosphates and 0.138 dialkyl phosphates. Conversion of the alcohol groups was over 90%.

EXAMPLE 3

Glyphosate Formulation Stability Evaluation

Rodeo, a trademark of the Monsanto Co. For a commercially available solution of glyphosate (N-phosphonomethyl glycine) in the form of its isopropylamine salt (53.8% conc. by wt), was blended with the product mixtures of Examples 1 and 2 and the stability of the solution with respect to phase separation under extreme temperature storage conditions was evaluated. The ester mixture of Example 1, with low dialkyl phosphate content, is primarily composed of compounds of the formula IV wherein $R_4$ is hydrogen, $R_5$ is OH, Y is hydrogen, t is 0 with either one or both hydroxyl groups converted to phosphate esters, w and w' equals 0 or 1 but both cannot be 0. The mixture of Example 2, with higher hydroxyl group conversion and higher dialkyl ester content, would have fewer hydroxyl groups remaining and over one-fourth of the amine starting material would be bound into phosphoamphoteric oligomers of the general structure I, where "m" is a low integer (1 or 2) with the remainder primarily being the mono- and di-phosphate esters of the fatty amine bis-ethoxylate.

TABLE 1

Glyphosate Formulations

| Component | Solution A | Solution B |
|---|---|---|
| Rodeo | 7.63 g | 7.63 g |
| Product from Ex. 1 | 1.00 g | |
| Product from Ex. 2 | | 1.17 g |
| Deionized Water | 1.37 g | 1.20 |

TABLE 2

Formulation Stability

| Formulation | 72 Hours at 55° C. | 72 Hours at 4° C. |
|---|---|---|
| A | No phase separation | No phase separation |
| B | No phase separation | No phase separation |

The compounds of Examples 1 and 2 passed both the high and low temperature stability evaluation in contrast to other anionic surfactant additives evaluated such as Rhodacal DSB a disodium dodecyl diphenyl oxide disulfonate, Rhodapon OLS a sodium octyl sulfate, Rhodapon CAV a sodium isodecyl sulfate, Rhodapex CO-436 an ammnonium nonyl phenol-4(EO) ethoxylate sulfate, Soprophor 4D384 an anmionium tristyrylphenol-16(EO) ethoxylate sulfate, (all of the aforementioned are trademarks of Rhodia Inc.), SXS-40 a 40% (aq.) sodium xylene sulfonate, an ethoxylated tall oil fatty acid, non-ionics such as di- and triethylene glycol, polyethylene glycol (400 mol. wt.), glycerine, Antarox 17-R-4 (EO/PO copolymer) a trademark of Rhodia Inc. For polypropylene oxide capped polyethylene glycol, reverse ethylene oxide/propylene oxide copolymer, and diethylene glycol monobutyl ether.

What is claimed is:

1. An aqueous composition comprising
   a) a bioactive compound
   b) a stabilizingly effective amount of a phosphate amphoteric surfactant of the general formula

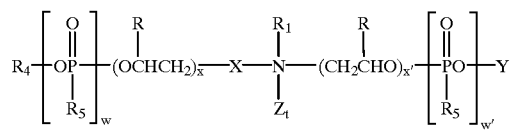

wherein X is

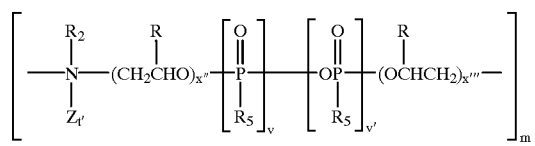

$R_1$ and $R_2$ independently are selected from the group consisting of substituted or unsubstituted $C_1$ to $C_{36}$ straight or branched chain alkyl, alkenyl, aryl, alkylaryl, arylalkyl and mixtures thereof, wherein $R_1$ and $R_2$ are optionally further characterized as containing ether, thioether, polyoxyalkylene oxide, amine, amine oxide, alkylamine, amide, alkylamide, carbonyl or ester groups, or are substituted thereby with open valences filled by $R_3$ wherein $R_3$ is hydrogen or $R_1$;

R independently is H, $C_{1-18}$ alkyl; alkenyl, aryl, alkylaryl, or arylalkyl;

$R_4$ is independently H, $C_{1-18}$ alkyl, alkenyl, aryl, alkylaryl, or arylalkyl;

$R_5$ is independently OH, OY, A, or $OR_4$ wherein A is

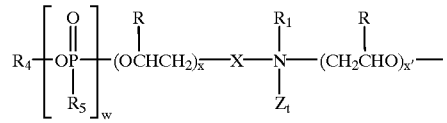

Y is H, or a counterion which, when needed to balance a charge, is an alkali metal, alkali earth metal, protonated amine, or quaternary ammonium counterion, Z is independently H, or oxygen;

t and t' are independently 0 or 1;

m is 0 to 10;

v is 1 and v' is independently 0 or 1;

w and w' are independently 0, 1 or 2 with the proviso that both are not equal to 0; and x, x', x", and x''' are independently 0 to 50 with the proviso that a nitrogen atom is not bonded directly to a phosphorus atom; and c) water.

2. The aqueous composition of claim 1 wherein the bioactive compound is ionic.

3. The aqueous composition of claim 1 wherein R and $R_1$ are individually

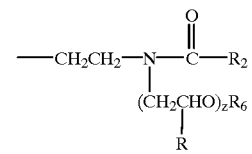

wherein $R_6$ is independently selected from the group consisting of H, or

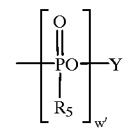

and z is 0 to 50.

4. The aqueous composition of claim 1 wherein the amphoteric surfactant is of the general formula

II

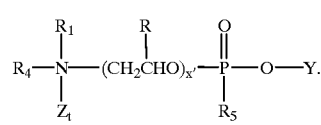

5. The aqueous composition of claim 1 wherein the amphoteric surfactant is of the general formula

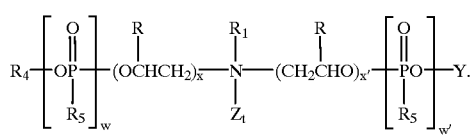

IV

6. The aqueous composition of claim 1 wherein the amphoteric surfactant is of the general formula

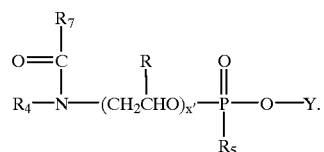

VI wherein:
$R_7$ is hydrogen or $C_1$–$C_{30}$ alkyl, alkenyl, aryl, alkaryl, or arylalkyl.

7. The aqueous composition of claim 1 wherein the amphoteric surfactant is of the general formula

VII

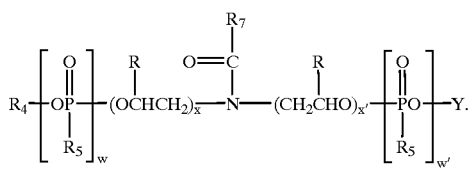

wherein:
$R_7$ is hydrogen or $C_1$–$C_{30}$ alkyl, alkenyl, aryl, alkaryl, or arylalkyl.

8. The aqueous composition of claim 1 wherein the amphoteric surfactant is of the general formula

VIII

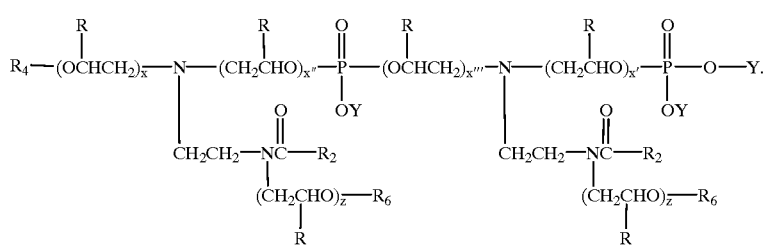

wherein: $R_1$ and $R_2$ are independently

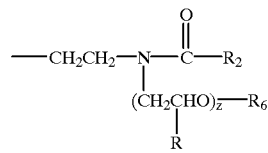

and z is 0 to 50.

9. The aqueous composition of claim 1 wherein the bioactive is a pesticide.

10. The aqueous composition of claim 9 wherein the pesticide is a herbicide.

11. The aqueous composition of claim 10 wherein the small ionic herbicide is N-phosphonomethyl glycine or a salt thereof.

12. An aqueous composition consisting essentially of
a) a bioactive compound
b) a stabilizingly effective amount of a phosphonate amphoteric surfactant of the general formula

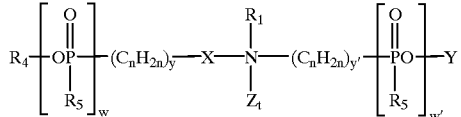

wherein X is

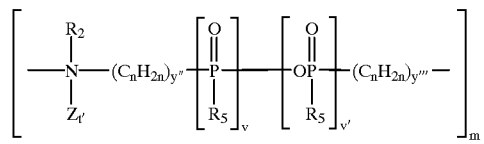

$R_1$ and $R_2$ independently, are selected from the group consisting of substituted or unsubstituted $C_1$ to $C_{36}$ straight or branched chain alkyl, alkenyl, aryl, alkylaryl, arylalkyl, and mixtures thereof, wherein said $R_1$ and $R_2$ are optionally further characterized as containing ether, thioether, polyoxyalkylene oxide, amine, amine oxide, amide alkylamine, alkylamide, carbonyl or ester groups, or are substituted thereby with open valences filled by $R_3$ wherein $R_3$ is hydrogen or $R_1$;

$R_4$ is independently H, $C_{1-18}$ alkyl, alkenyl, aryl, alkaryl, or arylalkyl;

$R_5$ is independently OH, OY, A, or $OR_4$ wherein A is

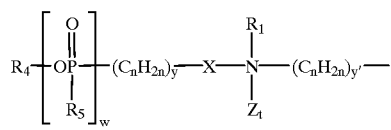

Y is H, or a counterion which, when needed to balance a charge, is an alkali metal, alkali earth metal, protonated amine, or quaternary ammonium counterion, Z is independently H, or oxygen;
n is independently a whole number from 2 to about 4;
t and t' are independently 0 or 1;
m is 0 to 10;
v is 1 and v' is independently 0 or 1;
w and w' are independently 0, 1 or 2 with the proviso that both are not equal to 0; and
y, y', y" and y'" are independently 0 or with the proviso that a nitrogen atom is not bonded directly to a phosphorus atom; and c) water.

13. The aqueous composition of claim 12 wherein the amphoteric surfactant is of the general formula

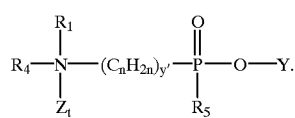

III

14. The aqueous composition of claim 12 wherein the amphoteric surfactant is of the general formula

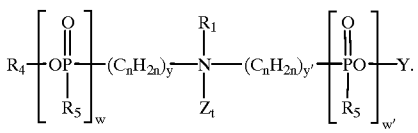

V

15. The aqueous composition of claim 12 wherein the bioactive is a pesticide.

16. The aqueous composition of claim 15 wherein the pesticide is a herbicide.

17. The aqueous composition of claim 16 wherein the herbicide is N-phosphonomethyl glycine or a salt thereof.

* * * * *